United States Patent
Gagos

(10) Patent No.: US 9,556,097 B2
(45) Date of Patent: Jan. 31, 2017

(54) PROCESS FOR THE PREPARATION OF XANTHOHUMOL

(71) Applicant: AXEN BIO GROUP SP. Z O.O., Sopot (PL)

(72) Inventor: Mariusz Gagos, Lubin (PL)

(73) Assignee: AXEN BIO GROUP SP. Z O.O., Sopot (PL)

( * ) Notice: Subject to any disclaimer, the term of this patent is extended or adjusted under 35 U.S.C. 154(b) by 0 days.

(21) Appl. No.: 15/027,004

(22) PCT Filed: Sep. 16, 2014

(86) PCT No.: PCT/IB2014/001872
§ 371 (c)(1),
(2) Date: Apr. 4, 2016

(87) PCT Pub. No.: WO2015/049561
PCT Pub. Date: Apr. 9, 2015

(65) Prior Publication Data
US 2016/0237014 A1    Aug. 18, 2016

(30) Foreign Application Priority Data
Oct. 4, 2013  (PL) .................................... 405540

(51) Int. Cl.
*C07C 45/85* (2006.01)
*C07C 45/79* (2006.01)
*C07C 45/86* (2006.01)

(52) U.S. Cl.
CPC .............. *C07C 45/85* (2013.01); *C07C 45/79* (2013.01); *C07C 45/86* (2013.01)

(58) Field of Classification Search
CPC ........... C07C 45/85; C07C 45/86; C07C 45/79

USPC .................................................... 568/324, 327
See application file for complete search history.

(56) References Cited

U.S. PATENT DOCUMENTS

| | | | |
|---|---|---|---|
| 2005/0042318 A1 | 2/2005 | Erdelmeier et al. | 424/778 |
| 2007/0254086 A1 | 11/2007 | Faltermeier et al. | 426/600 |
| 2009/0258094 A1 | 10/2009 | Ono et al. | 424/744 |

FOREIGN PATENT DOCUMENTS

| | | | | |
|---|---|---|---|---|
| CN | 101811950 A | 8/2005 | ............ | C07C 49/84 |
| CN | 101433592 A | 5/2009 | ............ | A61K 36/30 |
| CN | 101440029 A | 5/2009 | ............ | C07C 49/84 |
| DE | 199 39 350 A1 | 2/2001 | ............... | C12C 3/08 |
| EP | 1 424 385 131 | 11/2003 | ............... | C12C 3/10 |
| EP | 1 727 555 B1 | 12/2004 | ......... | A61K 36/185 |
| EP | 2 187 899 B1 | 8/2008 | .......... | A61K 35/185 |
| GB | 1 274 678 | 5/1972 | | |
| PL | 214468 B1 | 5/2009 | ............. | C07C 45/78 |

OTHER PUBLICATIONS

International Search Report in related application No. PCT/IB2014/001872 mailed Feb. 25, 2015.
Written Opinion in related application No. PCT/IB2014/001872 mailed Feb. 25, 2015.
Polish Search Report in related application No. P.405540 mailed Jan. 16, 2014.

*Primary Examiner* — Sikarl Witherspoon
(74) *Attorney, Agent, or Firm* — Renner Kenner Grieve Bobak Taylor & Weber

(57) ABSTRACT

The invention provides a process for the preparation of xanthohumol, wherein a xanthohumol-containing extract is mixed with water, a transition metal salt solution is added to the obtained mixture, and then the obtained xanthohumol precipitate is collected and dried to obtain xanthohumol of the purity higher than 90%.

15 Claims, No Drawings

PROCESS FOR THE PREPARATION OF XANTHOHUMOL

CROSS-REFERENCE TO RELATED APPLICATION

This is a §371 application of International Patent Application No. PCT/IB2014/001872, filed Sep. 16, 2014, which claims benefit of Polish Patent Application No. p. 405540, filed on Oct. 4, 2013, and which are incorporated herein by reference.

TECHNICAL FIELD

The invention provides a process for the preparation of high purity xanthohumol from post-extraction spent hops, granulated hop plant or hops. Due to the high purity of the obtained xanthohumol it could be successfully used in dietary supplements, beverages and as a therapeutic product ingredient.

Xanthohumol (Xn), or ((E)-1-[2,4-dihydroxy-6-methoxy-3-(3-methylbut-2-enyl)-phenyl]-3-(4-hydroxyphenyl)-prop-2-en-1-one) is a naturally-occurring compound of the group of prenylated chalcones, the main source of it being female inflorescence of *Humulus Lupus* (hop). It is present only in traces in the beer. The compound is composed of two benzene rings linked by the α,β-unsaturated carbonyl moiety:

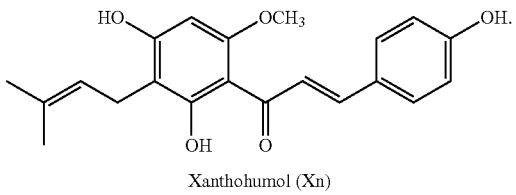 [SMILES: COc1cc(O)c(CC=C(C)C)c(O)c1C(=O)/C=C/c1ccc(O)cc1]

Xanthohumol (Xn)

The presence of a free hydroxy group in the molecule makes it easily isomerizable to the proper flavanone—an intermediate at the flavonoid biosynthesis pathway. As opposed to other ingredients of hops, xanthohumol is more lipophilic, the feature being connected with the presence of the prenylated substituent in its structure. It should be noted that in living biological systems, the prenylated (farnesyl or geranylgeranyl) moieties facilitate attachment of numerous intracellurar molecules to a cell membrane, determining their proper activities. Likewise, it is suggested that in the case of xanthohumol, such moieties can significantly modulate biological activity of the compound, and what is more, influence its physical-chemical properties and sub-cellular distribution.

In vitro and in vivo studies suggest also that xanthohumol reduces inflammatory and oxidative processes by means of various mechanisms. The leading ones are: elimination of oxygen free radicals and their reactive forms (RTF), cyclooxygenase (COX I and COX II) activity inhibition, reduction in prostaglandin, NO, TNFα, NFκB production and neutralization of membrane phospholipide peroxidation.

Antioxidative and antiinflammatory activity of xanthohumol is connected with the presence of the hydroxy groups and the prenylated substituent in its molecule. Of importance is also the α,β-unsaturated carbonyl moiety. The moiety participates in the Michel reaction with biologically important nucleophiles eg.: L-cysteine in proteins and other sulfhydryl group-containing molecules. In that way, covalent adducts which cause the loss of biological activity of various molecules bound by xanthohumol are obtained.

The broad spectrum of xanthohumol activity stems probably from the compound's ability to bind important biological molecules. One of the best known examples is the influence of xanthohumol on polymerase α synthetase, topoisomerase I, alkaline phosphatase, aromatase, diacylglycerol acyltransferase, MAPK signalling pathway proteins, FAK kinase, Akt and STAT or NF-κB transcription factors. Xn-induced reduction of activities of said proteins induces pleiotropic cell effects as a consequence of proliferation, cell cycle, adhesion and migration disturbances in tumorous cells.

Noteworthy is also information concerning its neuroprotective properties. In the rat model of MCAO-induced focal ischemia, which reflects focal brain ischemia in vivo, xanthohumol significantly reduces the brain ischemic necrosis area. Xanthohumol is thus suggested to reduce also a neurotoxic effect induced by the β-amyloid peptide (Aβ). Aβ is known to mediate the free-radical mechanism and is one of the main causes of Alzheimer's disease, by increasing production of free radicals and peroxidation of lipids in nerve cells, which consequently lead to their apoptosis.

Further, apart from its effect on receptors, the mechanism of xanthohumol's activity could be connected to its selective activity towards lipid membranes. Studies on mechanisms of interaction of xanthohumol with model lipid membranes indicate major modification of dynamic and structural properties of a membrane. Even very small concentrations of xanthohumol strongly interact with hydrophilic fragments of lipid membrane to influence bilayer thickness changes. It is also known that neonicotinoids, due to their high hydrophobicity, penetrate lipid membranes very easily. Interaction of xanthohumol with lipid membrane can significantly reduce its penetration by neonicotinoids, which could explain its strong activity, apart from blocking nicotine receptors.

Concerning its chemical structure, xanthohumol is a polyphenol, however, as opposed to polyphenols, it is scarcely soluble in hot water, but dissolves readily in alcohols or water/alcohol mixtures.

A good source of xanthohumol is the post-extraction spent hops, which comprises wastes from the production of hop extract used by brewing industry for the manufacture of beer. The post-extraction spent hops are estimated to contain up to 1% of xanthohumol, depending on the species of a hop plant.

BACKGROUND ART

Numerous technologies for the preparation of xanthohumol are known in the art. The application DE 199 39 350 A1 describes a process for the preparation of a xanthohumol-enriched hop extract, wherein mixtures of water and ethanol were used for extraction. The obtained extract contained 5 to 15% of xanthohumol.

The patent EP 1 424 385 B1 discloses a method of extracting xanthohumol from the raw xanthohumol-containing material by use of compressed $CO_2$ as a solvent under a pressure above 500 bar and at temperatures above 60° C.

The application CN 101440029 discloses a method of extracting xanthohumol from the hop plant and xanthohumol-containing products, wherein the extraction with an organic solvent assisted by ultrasounds is conducted, followed by mixing with diatomite, filtering, washing out with water/methanol mixture, concentrating, precipitating and drying to obtain xanthohumol of the 86% purity.

The patent EP 2 187 899 B1 discloses a process for the preparation of a composition of the high xanthohumol content from a hop plant, wherein a salt is added to a xanthohumol-containing solution to the concentration in the range of from 0.05 to 5.0M, followed by increasing pH to from 10.5 to 12.0, filtering the obtained precipitate, acidifying the filtrate to pH 7-8 to obtain the xanthohumol precipitate of the 40-95% purity.

The patent application U.S. Ser. No. 11/790,365 discloses a process for the preparation of the powder of the high (60-90%) xanthohumol content, comprising suspending a xanthohumol-enriched extract in an alkaline solution, separating insoluble products, neutralizing and precipitating the dissolved xanthohumol with an acid and isolating the product.

Patent CN 101433592 discloses use of various adsorption resins to prepare high purity xanthohumol.

In conclusion, analysis of the prior art discloses unequivocally that there is a need for developing a simple and inexpensive process for the preparation of high purity xanthohumol.

SUMMARY OF THE INVENTION

The problem is solved by a newly developed process for the preparation of xanthohumol from post-extraction spent hops, granulated hop plant or hops.

Thus, the invention relates to a process for the preparation of xanthohumol, wherein:
a) a xanthohumol-containing extract is mixed with water;
b) a transition metal salt solution is added to the obtained mixture;
c) the obtained xanthohumol precipitate is collected and dried to obtain xanthohumol of the purity higher than 90%.

Preferably, in step b) the concentration of the salt in the mixture is adjusted within the range of from 0.001M to 10M, more preferably in step b) the concentration of the salt in the mixture is adjusted within the range of from 0.001M do 0.05M or above 5M.

Preferably, additionally after the salt is added in step b:
b1) the solution is alkalized to the pH level above 7;
b2) the first precipitate is filtered off, and the filtrate is acidified to the pH level below 7;
b3) the acidified filtrate is concentrated to obtain the xanthohumol precipitate.

Preferably, in step b1) the solution is alkalized to the pH level in the range of 7.5 do 10.5 or above 12.

Preferably, the xanthohumol-containing extract is obtained by extraction of the post-extraction spent hops, hops, granulated hop plant or a mixture thereof with an organic water-miscible solvent, the solvent being used in an amount of from 0.1 to 10 liters per 1 kg of the raw material.

Preferably, as an organic water-miscible solvent, ketones and alcohols or a mixture thereof is used, more preferably, as an organic water-miscible solvent acetone, methanol, ethanol, propanol or a mixture thereof is used.

Preferably, the extraction is conducted at a temperature in the range of from 5 to 65° C.

Preferably, the xanthohumol-containing extract is mixed with water at a ratio in the range of from 0.1 to 5 liters of water per 1 liter of the extract, more preferably the xanthohumol-containing extract is mixed with water at a ratio in the range of from 1 to 3 liters of water per 1 liter of the extract.

Preferably, in step b) a concentration of a transition metal salt is provided within the range of from 0.01M to 0.05M.

Preferably, as a transition metal salt a copper(II) salt or a zinc(II) salt is used.

Preferably, as a transition metal salt a chloride salt, a nitrate salt, or a sulfate salt is used.

Preferably, as a transition metal salt copper(II) chloride, copper(II) sulfate or zinc(II) chloride or zinc(II) sulfate is used.

BEST MODE FOR CARRYING OUT THE INVENTION

The process according to the invention allows to obtain xanthohumol of the purity of at least 90% (usually above 95%) in a good yield. The process according to the invention do not require use of complex chromatography systems or supported resins.

Purity of the obtained xanthohumol was determined by the HPLC technique on the SUPELCOSIL LC-PAH column of 15 cm×4.6 mm, 5 µm grain size, column temperature of 20° C., Phase A—95% acetonitrile 0.3% HCOOH; Phase B—2% acetonitrile 0.3% HCOOH, 2 ml/min flow rate, 20 µl injection, detection at the wavelength of 370 and 290 nm.

The invention was illustrated by the following working examples.

Example 1

250 g of post-extraction spent hops were weighed out and poured over with acetone (0.75 L). After mechanical stirring for 1 h the extract formed was filtered through a filter paper. The obtained filtrate (0.65 L) was flushed with water (1.3 L). Then the solution was added with an aqueous solution of $CuCl_2$ (the concentration of 10 g/l) at the volume of 300 ml per 1 liter of the filtrate (the final concentration of 0.022M). After adding copper chloride, the pH of the solution was stabilized at ~4.5. Practically immediately after copper chloride pouring, precipitation in the extract occurred of agglomerates of a green substance of residual humulons and chlorophyll separating from a yellow solution where xanthohumol was found. After an hour, NaOH was added to precipitate an excess of copper by raising the pH to about 10. After 1 h, precipitation was observed of a muddy mass and copper hydroxide precipitate at the bottom of the vessel. The precipitates were filtered off on a filter paper. The obtained filtrate was acidified with HCl to pH 6 and concentrated on a rotary evaporator to yield a crystalline xanthohumol precipitate which was filtered off and dried in an oven (temperature of 50-60° C.) to give 206 mg of xanthohumol of 97.8% HPLC purity. The yield of the xanthohumol extraction process was 82% based on the total content of xanthohumol in the spent hops.

Example 2

Xanthohumol was obtained as in Example 1, except that after adding copper chloride, the precipitated green sludge was filtered off and the filtrate was concentrated on a rotary evaporator to yield the crystalline xanthohumol precipitate of the 90.8% HPLC purity.

Example 3

Xanthohumol was obtained as in Example 1, except that copper chloride was substituted by a zinc sulfate ($ZnSO_4$) solution at the concentration of 10 g/l. After addition of the zinc salt solution, the pH of the solution was stabilized at ~6, and precipitation was observed. After about an hour NaOH was added with the pH increase to about 10. After 1 h further precipitate was observed at the bottom of the vessel. The precipitate was filtered off on a filter paper. The obtained filtrate was acidified with HCl do pH 6 and concentrated on a rotary evaporator to yield the crystalline xanthohumol precipitate, which was filtered off and dried in an oven (the temperature of 50-60° C.) to give xanthohumol of the 97.8% HPLC purity with the 79% yield based on the total content of xanthohumol in the spent hops.

Example 4

250 g of post-extraction spent hops were weighed out and poured over with 0.75 liters of pure methanol. After mechanical stirring for 1 h the formed extract was filtered on a filter paper. The obtained filtrate was poured over with water in a volume ratio of 1:2 (one part of the filtrate to two parts of water). Then the solution was added with the aqueous solution of $CuCl_2$ (at the concentration of 10 g/l) in a volume of 300 ml per 1 liter of the filtrate (the final concentration of the salt of 0.022M). After 1 h, precipitation in the extract was observed of agglomerates of a green substance separating from a yellow solution. NaOH was then added to raise the pH to 10. After 1 h, a muddy green precipitate was observed at the bottom of the vessel. The formed extract was filtered on a filter paper. The obtained extract was acidified with HCl to pH 6. The remaining amounts of the solvent were removed on an evaporator and a suspension of xanthohumol crystals was obtained. The suspension was filtered through a filter paper to yield xanthohumol, which was dried in an oven at 55° C. to give 196 mg of xanthohumol of the 95.8% purity with the yield of about 78% based on the total content of xanthohumol in the spent hops.

Example 5

Xanthohumol was obtained as in Example 4, except that instead copper(II) chloride, copper(II) sulfate ($CuSO_4$) was used at the concentration of 10 g/l and xanthohumol was obtained with the 94.8% purity.

Example 6

Xanthohumol was obtained as in Example 1, except that higher concentrations of copper(II) chloride were used—in the range of 0.022M to 0.044M. Xanthohumol was obtained with the purity ranging from 96.3-97.8%.

Example 7

Xanthohumol was obtained as in Example 1, except that the ratio of the extract from the first step to the amount of ware added of 1:1 and the $CuCl_2$ concentration of 0.022M were used, to yield xanthohumol of the 96.8% purity.

Example 8

Xanthohumol was obtained as in Example 1, except that 2-propanol in place of acetone and the $CuCl_2$ concentration of 0.022M were used to yield xanthohumol with the 93.8% purity.

Comparative Example 1

250 g of post-extraction spent hops were weighed out and poured over with acetone (0.75 L). After mechanical stirring for 1 h the extract formed was filtered through a filter paper. The obtained filtrate was concentrated to yield xanthohumol of the 32.8% purity.

Comparative Example 2

250 g of post-extraction spent hops were weighed out and poured over with acetone (0.75 L). After mechanical stirring for 1 h the extract formed was filtered through a filter paper. The obtained filtrate (0.65 l) was poured over with water (1.3 l). Then the solution was added with the aqueous solution of NaCl (at the concentration of 30 g/l) at the volume of 300 ml per 1 liter of the filtrate. Then, NaOH was added to raise the pH to about 12. The precipitate formed was filtered off through a filter paper. The obtained filtrate was acidified with HCl to pH 5 and concentrated on a rotary evaporator to obtain a xanthohumol precipitate, which was filtered off and dried in an oven (the temperature of 50-60° C.) to yield xanthohumol of the 84.8% HPLC purity.

Comparative Example 3

Xanthohumol was obtained as in Comparative Example 2, except that NaCl was not used. Xanthohumol was obtained of the 58% HPLC purity—as a result of alkalization to pH 12 only.

Based on the above-described working examples, it could be ascertained that the process according to the invention allows to obtain xanthohumol of a high purity by an exceptionally simple and inexpensive process. It is obvious for a person skilled in the art that xanthohumol obtained by the inventive process could be further purified according to known methods.

The invention claimed is:

1. A process for the preparation of xanthohumol, characterized in that:
    a) a xanthohumol-containing extract is mixed with water;
    b) a transition metal salt solution is added to the obtained mixture;
    c) the obtained xanthohumol precipitate is collected and dried to obtain xanthohumol of the purity higher than 90%.

2. The process of claim 1, characterized in that in step b) the concentration of the salt in the mixture is adjusted within the range of from 0.001M to 10M.

3. The process of claim 2, characterized in that in step b) the concentration of the salt in the mixture is adjusted within the range of from 0.001M to 0.05M.

4. The process of claim 1, characterized in that further after adding the salt in step b:
    b1) the solution is alkalized to the pH level above 7;
    b2) the first precipitate is filtered off, and the filtrate is acidified to the pH level below 7;
    b3) the acidified filtrate is concentrated to obtain the xanthohumol precipitate.

5. The process of claim 4, characterized in that in step b1) the solution is alkalized to the pH level in the range of from 7.5 to 10.5.

6. The process of claim 1, characterized in that the xanthohumol-containing extract is obtained by extraction of post-extraction spent hops, hops, granulated hop plant or a mixture thereof with an organic water-miscible solvent, said solvent being used in an amount of from 0.1 to 10 liters per 1 kg of the raw material.

7. The process of claim 6, characterized in that as an organic water-miscible solvent, ketones and alcohols or a mixture thereof are used.

8. The process of claim 7, characterized in that as an organic water-miscible solvent, acetone, methanol, ethanol, propanol or a mixture thereof is used.

9. The process of claim 1, characterized in that the extraction is conducted at a temperature in the range of from 5 to 65° C.

10. The process of claim 1, characterized in that the xanthohumol-containing extract is mixed with water at a ratio in the range of from 0.1 to 5 liters of water per 1 liter of the extract.

11. The process of claim 10, characterized in that the xanthohumol-containing extract is mixed with water at a ratio in the range of from 1 to 3 liters of water per 1 liter of the extract.

12. The process of claim 1, characterized in that in step b) the concentration of a transition metal salt is provided within the range of from 0.01M to 0.05M.

13. The process of claim 1, characterized in that as a transition metal salt, a copper(II) salt or a zinc(II) salt is used.

14. The process of claim 1, characterized in that as a transition metal salt, a chloride salt, a nitrate salt, or a sulfate salt is used.

15. The process of claim 1, characterized in that as a transition metal salt, copper(II) chloride, copper(II) sulfate or zinc(II) chloride or sulfate zinc (II) is used.

\* \* \* \* \*